US012589165B2

(12) United States Patent
de los Pinos et al.

(10) Patent No.: US 12,589,165 B2
(45) Date of Patent: Mar. 31, 2026

(54) METHODS FOR TREATING BLADDER TUMORS WITH VIRAL NANOPARTICLE CONJUGATES AND IMMUNE CHECKPOINT INHIBITORS

(71) Applicants: Aura Biosciences, Inc., Cambridge, MA (US); The United States of America, as represented by the Secretary, Department of Health and Human Services, Bethesda, MD (US)

(72) Inventors: Elisabet de los Pinos, Brookline, MA (US); John Todd Schiller, Kensington, MD (US); Rhonda C. Kines, Washington, DC (US)

(73) Assignees: The United States of America, as represented by the Secretary, Department of Health and Human Services, Bethesda, MD (US); Aura Biosciences, Inc., Boston, MA (US)

( * ) Notice: Subject to any disclaimer, the term of this patent is extended or adjusted under 35 U.S.C. 154(b) by 1341 days.

(21) Appl. No.: 16/604,790

(22) PCT Filed: Apr. 11, 2018

(86) PCT No.: PCT/US2018/027080
§ 371 (c)(1),
(2) Date: Aug. 16, 2021

(87) PCT Pub. No.: WO2018/191363
PCT Pub. Date: Oct. 18, 2018

(65) Prior Publication Data
US 2021/0290778 A1    Sep. 23, 2021
US 2022/0152217 A9    May 19, 2022

Related U.S. Application Data

(60) Provisional application No. 62/484,693, filed on Apr. 12, 2017.

(51) Int. Cl.
| | |
|---|---|
| *A61K 47/69* | (2017.01) |
| *A61K 39/00* | (2006.01) |
| *A61K 39/395* | (2006.01) |
| *A61K 41/00* | (2020.01) |
| *A61P 35/00* | (2006.01) |
| *C12N 7/00* | (2006.01) |

(52) U.S. Cl.
CPC ...... *A61K 47/6901* (2017.08); *A61K 39/3955* (2013.01); *A61K 41/0061* (2013.01); *A61K 41/0071* (2013.01); *A61K 41/0076* (2013.01); *A61P 35/00* (2018.01); *C12N 7/00* (2013.01); *A61K 2039/54* (2013.01); *A61K 2039/545* (2013.01); *C12N 2710/20023* (2013.01); *C12N 2710/20042* (2013.01); *C12N 2710/20071* (2013.01)

(58) Field of Classification Search
CPC ............ A61K 47/6901; A61K 39/3955; A61K 41/0061; A61K 41/0071; A61K 41/0076; A61K 2039/54; A61K 2039/545; A61K 39/39558; A61K 45/06; A61K 47/62; A61K 39/395; A61P 35/00; C12N 7/00; C12N 2710/20023; C12N 2710/20042; C12N 2710/20071; C07K 16/2818; C07K 16/2827; B82Y 5/00
See application file for complete search history.

(56) References Cited

U.S. PATENT DOCUMENTS

| | | | |
|---|---|---|---|
| 4,625,014 | A | 11/1986 | Senter et al. |
| 4,659,839 | A | 4/1987 | Nicolotti |
| 5,126,129 | A | 6/1992 | Wiltrout et al. |
| 5,290,551 | A | 3/1994 | Berd |
| 5,334,711 | A | 8/1994 | Sproat |
| 5,478,556 | A | 12/1995 | Elliott et al. |
| 5,667,764 | A | 9/1997 | Kopia et al. |
| 5,716,824 | A | 2/1998 | Beigelman |
| 6,022,522 | A | 2/2000 | Sweet et al. |
| 6,180,389 | B1 | 1/2001 | Douglas et al. |
| 6,416,945 | B1 | 7/2002 | McCarthy et al. |
| 6,599,739 | B1 | 7/2003 | Lowy et al. |
| 6,719,958 | B1 | 4/2004 | Gozzini et al. |
| 6,984,386 | B2 | 1/2006 | Douglas et al. |
| 6,991,795 | B1 | 1/2006 | Lowe et al. |
| 7,205,126 | B2 | 4/2007 | Qiao et al. |

(Continued)

FOREIGN PATENT DOCUMENTS

| | | |
|---|---|---|
| CN | 1904012 A | 1/2007 |
| CN | 102481378 A | 5/2012 |

(Continued)

OTHER PUBLICATIONS

Gao et al., Enhanced Anti-Tumor Efficacy through a Combination of Integrin αvβ6-Targeted Photodynamic Therapy and Immune Checkpoint Inhibition. Theranostics. Mar. 3, 2016;6(5):627-37. doi. 10.7150/thno.14792.
Huis In't Veld et al., Immune checkpoint inhibition combined with targeted therapy using a novel virus-like drug conjugate induces complete response in a murine model of local and distant tumors. Cancer Immunol Immunother. Jul. 2023;72(7):2405-2422. doi: 10.1007/s00262-023-03425-3. Epub Mar. 30, 2023.

(Continued)

*Primary Examiner* — Alana Harris Dent
(74) *Attorney, Agent, or Firm* — Wolf, Greenfield & Sacks, P.C.

(57) ABSTRACT

Some embodiments of the present disclosure are directed to methods and compositions for the treatment of tumors, using a combination of immunotherapeutic agents and tumor-targeting viral capsid protein assemblages comprising anti-cancer molecules conjugated to viral capsid proteins.

20 Claims, 6 Drawing Sheets

(56) References Cited

U.S. PATENT DOCUMENTS

| | | | |
|---|---|---|---|
| 7,351,533 | B2 | 4/2008 | McCarthy et al. |
| 7,951,379 | B2 | 5/2011 | Kuroda et al. |
| 8,394,411 | B2 | 3/2013 | Roberts et al. |
| 9,700,639 | B2 | 7/2017 | de los Pinos et al. |
| 9,724,404 | B2 | 8/2017 | Coursaget et al. |
| 9,855,347 | B2 | 1/2018 | de los Pinos et al. |
| 10,117,947 | B2 | 11/2018 | de los Pinos et al. |
| 10,179,168 | B2 | 1/2019 | Coursaget et al. |
| 10,300,150 | B2 | 5/2019 | de los Pinos et al. |
| 10,588,984 | B2 | 3/2020 | de los Pinos et al. |
| 10,596,275 | B2 | 3/2020 | de los Pinos et al. |
| 10,688,172 | B2 | 6/2020 | Coursaget et al. |
| 11,110,181 | B2 | 9/2021 | de los Pinos et al. |
| 11,141,483 | B2 | 10/2021 | Makings et al. |
| 11,154,620 | B2 | 10/2021 | Garcia-Guzman et al. |
| 11,806,406 | B2 | 11/2023 | de los Pinos et al. |
| 12,029,794 | B2 | 7/2024 | de los Pinos et al. |
| 2003/0129583 | A1 | 7/2003 | Martin |
| 2003/0206887 | A1 | 11/2003 | Morrissey et al. |
| 2004/0005338 | A1 | 1/2004 | Bachmann et al. |
| 2004/0028694 | A1 | 2/2004 | Young et al. |
| 2004/0115132 | A1 | 6/2004 | Young et al. |
| 2004/0121465 | A1 | 6/2004 | Robinson |
| 2004/0146531 | A1 | 7/2004 | Antonsson et al. |
| 2004/0152181 | A1 | 8/2004 | McCarthy et al. |
| 2005/0112141 | A1 | 5/2005 | Terman |
| 2005/0118191 | A1 | 6/2005 | Robinson et al. |
| 2005/0181064 | A1 | 8/2005 | Kuroda |
| 2006/0088536 | A1 | 4/2006 | Kuroda |
| 2006/0141042 | A1 | 6/2006 | Kuroda |
| 2006/0166913 | A1 | 7/2006 | Suzuki |
| 2006/0204444 | A1 | 9/2006 | Young et al. |
| 2006/0216238 | A1 | 9/2006 | Manchester et al. |
| 2006/0269954 | A1 | 11/2006 | Lowy et al. |
| 2007/0059245 | A1 | 3/2007 | Young et al. |
| 2007/0059746 | A1 | 3/2007 | Kuroda |
| 2007/0243157 | A1 | 10/2007 | Tanaka et al. |
| 2007/0258889 | A1 | 11/2007 | Douglas et al. |
| 2009/0012022 | A1 | 1/2009 | Milner et al. |
| 2009/0041671 | A1 | 2/2009 | Young et al. |
| 2010/0003326 | A1 | 1/2010 | Vertommen et al. |
| 2010/0135902 | A1 | 6/2010 | Roberts et al. |
| 2010/0189641 | A1 | 7/2010 | Chang et al. |
| 2011/0009601 | A1 | 1/2011 | Yamauchi et al. |
| 2011/0052496 | A1 | 3/2011 | Cid-Arregui |
| 2011/0065173 | A1 | 3/2011 | Kingsman et al. |
| 2011/0104051 | A1 | 5/2011 | Francis et al. |
| 2012/0015899 | A1 | 1/2012 | Lomonossoff et al. |
| 2012/0171290 | A1 | 7/2012 | Coursaget et al. |
| 2012/0207840 | A1 | 8/2012 | Aura |
| 2013/0071414 | A1 | 3/2013 | Dotti et al. |
| 2013/0115247 | A1 | 5/2013 | de los Pinos et al. |
| 2013/0116408 | A1 | 5/2013 | de los Pinos |
| 2013/0136689 | A1 | 5/2013 | Rohlff et al. |
| 2013/0202645 | A1 | 8/2013 | Barner et al. |
| 2014/0306869 | A1 | 10/2014 | Fujita et al. |
| 2014/0377170 | A1 | 12/2014 | de los Pinos et al. |
| 2015/0232880 | A1 | 8/2015 | Hemminki et al. |
| 2016/0024469 | A1 | 1/2016 | Wu |
| 2016/0228568 | A1 | 8/2016 | de los Pinos et al. |
| 2017/0274099 | A1 | 9/2017 | de los Pinos et al. |
| 2017/0368162 | A1 | 12/2017 | Coursaget et al. |
| 2018/0110883 | A1 | 4/2018 | de los Pinos et al. |
| 2018/0311269 | A1 | 11/2018 | Lobb et al. |
| 2018/0311374 | A1 | 11/2018 | Lobb et al. |
| 2019/0083647 | A1 | 3/2019 | de los Pinos et al. |
| 2019/0142925 | A1 | 5/2019 | Coursaget et al. |
| 2019/0275176 | A1 | 9/2019 | de los Pinos et al. |
| 2020/0188529 | A1 | 6/2020 | de los Pinos et al. |
| 2021/0393797 | A1 | 12/2021 | de los Pinos et al. |
| 2022/0088216 | A1 | 3/2022 | de los Pinos et al. |
| 2022/0387619 | A2 | 12/2022 | de los Pinos et al. |
| 2024/0216527 | A1 | 7/2024 | de los Pinos et al. |

FOREIGN PATENT DOCUMENTS

| | | | | |
|---|---|---|---|---|
| CN | 102573910 | A | 7/2012 | |
| CN | 105979967 | A | 9/2016 | |
| EP | 1491210 | A1 | 12/2004 | |
| JP | 2005-527493 | A | 9/2005 | |
| JP | 2007-65646 | A | 3/2007 | |
| JP | 2009-532564 | | 9/2009 | |
| JP | 2012-523455 | A | 10/2012 | |
| JP | 2016-531591 | A | 10/2016 | |
| WO | WO 91/03162 | A1 | 3/1991 | |
| WO | WO 92/07065 | A1 | 4/1992 | |
| WO | WO 93/15187 | A1 | 8/1993 | |
| WO | WO 97/26270 | A2 | 7/1997 | |
| WO | WO 99/15630 | A1 | 4/1999 | |
| WO | WO 00/09673 | A1 | 2/2000 | |
| WO | WO 01/55393 | A2 | 8/2001 | |
| WO | WO 03/008573 | A2 | 1/2003 | |
| WO | WO 03/061696 | A2 | 7/2003 | |
| WO | WO 2005/051431 | A1 | 6/2005 | |
| WO | WO 2005/086667 | A2 | 9/2005 | |
| WO | WO 2006/125997 | A1 | 11/2006 | |
| WO | WO 2008/048288 | A2 | 4/2008 | |
| WO | WO 2008/054184 | A1 | 5/2008 | |
| WO | WO 2008/103920 | A2 | 8/2008 | |
| WO | WO 2008/140961 | A2 | 11/2008 | |
| WO | WO 2010/027827 | A2 | 3/2010 | |
| WO | WO 2010/120266 | A1 | 10/2010 | |
| WO | WO 2011/039646 | A2 | 4/2011 | |
| WO | WO 2013/009717 | A1 | 1/2013 | |
| WO | WO 2013/080187 | A1 | 6/2013 | |
| WO | WO 2013/119877 | A1 | 8/2013 | |
| WO | WO 2014/039523 | A1 | 3/2014 | |
| WO | WO 2015/042325 | A1 | 3/2015 | |
| WO | WO 2015/075468 | A1 | 5/2015 | |
| WO | WO 2015/120363 | A1 | 8/2015 | |
| WO | WO 2015/142675 | A2 | 9/2015 | |
| WO | WO 2016/139362 | A1 | 9/2016 | |
| WO | WO 2017/031367 | A1 | 2/2017 | |
| WO | WO-2017075399 | A1 * | 5/2017 | ............ A61K 35/76 |
| WO | WO 2018/191363 | A1 | 10/2018 | |

OTHER PUBLICATIONS

Kines et al., Virus-Like Particle-Drug Conjugates Induce Protective, Long-lasting Adaptive Antitumor Immunity in the Absence of Specifically Targeted Tumor Antigens. Cancer Immunol Res. Jun. 2021;9(6):693-706. doi. 10.1158/2326-6066.CIR-19-0974. Epub Apr. 14, 2021.

Shitara K., Clinical Trials of Combination Therapy to Potentiate Efficacy of Immune Check Point Inhibitors. Int J Clin Exp Med. Jul. 30, 2016;258(5):471-479.

Extended European Search Report for Application No. EP 18783979.0 mailed Dec. 7, 2020.

Blackhall et al., Heparan sulfate proteoglycans and cancer. Br J Cancer. Oct. 19, 2001;85(8):1094-8. doi: 10.1054/bjoc.2001.2054.

Davies et al., Distribution and clinical significance of heparan sulfate proteoglycans in ovarian cancer. Clin Cancer Res. Aug. 1, 2004;10(15):5178-86. doi:10.1158/1078-0432.CCR-03-0103.

Mitsunaga et al., Cancer cell-selective in vivo near infrared photoimmunotherapy targeting specific membrane molecules. Nat Med. Nov. 6, 2011;17(12):1685-91. doi: 10.1038/nm.2554.

Sanderson, Heparan sulfate proteoglycans in invasion and metastasis. Semin Cell Dev Biol. Apr. 2001;12(2):89-98. doi: 10.1006/scdb.2000.0241.

International Preliminary Report on Patentability mailed Aug. 18, 2011 for Application PCT/IB2010/002654.

International Search Report and Written Opinion mailed Jun. 28, 2018 for Application PCT/US2018/027080.

International Preliminary Report on Patentability mailed Oct. 24, 2019 for Application PCT/US2018/027080.

[No Author Listed] Bac-to-Bac Baculovirus Expression System. An efficient site-specific transposition system to generate baculovirus for high-level expression of recombinant proteins. Sep. 4, 2010. Retrieved from the Internet on Sep. 23, 2013. 80 pages.

(56)                References Cited

OTHER PUBLICATIONS

[No Author Listed] GenBank Accession No. P03101, Major Capsid Protein L1, Jan. 11, 2011.

Alvarez, Insertion de sequences peptidiques dans la proteine majeure de capside du papillomavirus de type 16: application au ciblage pulmonaire de vecteurs derives et a la production d'un vaccine chimerique. Thesis. Universite Francois Rabelais. Jun. 20, 2006. 203 pages.

Bergsdorf et al., Highly efficient transport of carboxyfluorescein diacetate succinimidyl ester into COS7 cells using human papillomavirus-like particles. FEBS Lett. Feb. 11, 2003;536(1-3): 120-4.

Bousarghin et al., Inhibition of cervical cancer cell growth by human papillomavirus virus-like particles packaged with human papillomavirus oncoprotein short hairpin RNAs. Mol Cancer Ther. Feb. 2009;8(2):357-65. Epub Jan. 27, 2009.

Brasch et al., Encapsulation of phthalocyanine supramolecular stacks into virus-like particles. J Am Chem Soc. May 11, 2011;133(18):6878-81. doi: 10.1021/ja110752u. Epub Apr. 20, 2011.

Brumfield et al., Heterologous expression of the modified coat protein of Cowpea chlorotic mottle bromovirus results in the assembly of protein cages with altered architectures and function. J Gen Virol. Apr. 2004;85(Pt 4):1049-53.

Buck et al., Efficient intracellular assembly of papillomaviral vectors. J Virol. Jan. 2004;78(2):751-7.

Buck et al., Production of papillomavirus-based gene transfer vectors. Current Protocols in Cell Biology. 26.1.1-26.1.19, Dec. 2007.

Butz et al., siRNA targeting of the viral E6 oncogene efficiently kills human papillomavirus-positive cancer cells. Oncogene. Sep. 4, 2003;22(38):5938-45.

Canti et al., Photodynamic therapy with photoactivated aluminum disulfonated phthalocyanine and cellular immune response. Proc. SPIE 3254, Laser-Tissue Interaction IX (May 13, 1998); doi: 10.1117/12.308158. Event: BIOS '98 International Biomedical Optics Symposium, 1998, San Jose, CA, United States. Retrieved from the Internet: https://www.spiedigitallibrary.org/conference-proceedings-of-spie on Jul. 19, 2019. 8 pages.

Carpentier et al. Mutations on the FG surface loop of human papillomavirus type 16 major capsid protein affect recognition by both type-specific neutralizing antibodies and cross-reactive antibodies. J Med Viral. Dec. 2005;77(4):558-65. Abstract only.

Carpentier et al., Cell targeting for CF gene therapy: Identification of a new specific cell ligand and selection of infectious papillomavirus mutants. J Cystic Fibro. Jun. 1, 2009;8:S31.

Carpentier, Retargeting human papillomavirus-mediated gene transfer to human airway epithelial cells. J Cystic Fibro. Jun. 1, 2010;9:S17.

Carter et al., Identification of a human papillomavirus type 16-specific epitope on the C-terminal arm of the major capsid protein L1. J Virol. Nov. 2003;77(21):11625-32.

Carter et al., Identification of human papillomavirus type 16 L1 surface loops required for neutralization by human sera. J Virol. May 2006;80(10):4664-72.

Christensen et al. Surface conformational and linear epitopes on HPV-16 and HPV-18 L1 virus-like particles as defined by monoclonal antibodies. Virology. Sep. 1, 1996;223(1):174-84.

Cohen et al., Targeted in vitro photodynamic therapy via aptamer-labeled, porphyrin-loaded virus capsids. J Photochem Photobiol B. Apr. 5, 2013;121:67-74. doi: 10.1016/j.jphotobiol.2013.02.013. Epub Feb. 28, 2013.

Combita et al., Gene transfer using human papillomavirus pseudovirions varies according to virus genotype and requires cell surface heparan sulfate. FEMS Microbiol Lett. Oct. 16, 2001;204(1):183-8.

Cook et al., Purification of virus-like particles of recombinant human papillomavirus type 11 major capsid protein L1 from Saccharomyces cerevisiae. Protein Expr Purif. Dec. 1999;17(3):477-84.

Culp et al., Papillomavirus particles assembled in 293TT cells are infectious in vivo. J Virol. Nov. 2006;80(22):11381-4. Epub Aug. 30, 2006.

Douglas et al., Protein engineering of a viral cage for constrained nanomaterials synthesis. Adv Mater. Mar. 12, 2002;14(6):415-8.

Elbashir et al., Analysis of gene function in somatic mammalian cells using small interfering RNAs. Methods. Feb. 2002;26(2):199-213.

Ewers et al., GM1 structure determines SV40-induced membrane invagination and infection. Nat Cell Biol. Jan. 2010;12(1):11-20; sup pp. 1-12. doi: 10.1038/ncb1999. Epub Dec. 20, 2009.

Finnen et al., Interactions between papillomavirus L1 and L2 capsid proteins. J Viral. Apr. 2003;77(8):4818-26.

Feltkamp et al., Vaccination with cytotoxic T lymphocyte epitope-containing peptide protects against a tumor induced by human papillomavirus type 16-transformed cells. Eur J Immunol. Sep. 1993;23(9):2242-9.

Fleury et al., Identification of neutralizing conformational epitopes on the human papillomavirus type 31 major capsid protein and functional implications. Protein Sci. Jul. 2009;18(7):1425-38.

Gaden et al., Gene transduction and cell entry pathway of fiber-modified adenovirus type 5 vectors carrying novel endocytic peptide ligands selected on human tracheal glandular cells. J Virol. Jul. 2004;78(13):7227-47.

Gillitzer et al., Controlled ligand display on a symmetrical protein-cage architecture through mixed assembly. Small. Aug. 2006;2(8-9):962-6.

Hagensee et al. Self-assembly of human papillomavirus type 1 capsids by expression of the L1 protein alone or by coexpression of the L1 and L2 capsid proteins. Journal of virology. Jan. 1, 1993;67(1):315-22.

Jiang et al., Gel-based application of siRNA to human epithelial cancer cells induces RNAi-dependent apoptosis. Oligonucleotides. 2004 Winter;14(4):239-48.

Jiang et al., Selective silencing of viral gene E6 and E7 expression in HPV-positive human cervical carcinoma cells using small interfering RNAs. Methods Mol Biol. 2005;292:401-20.

Jiang et al., Selective silencing of viral gene expression in HPV-positive human cervical carcinoma cells treated with siRNA, a primer of RNA interference. Oncogene. Sep. 5, 2002;21(39):6041-8.

Jost et al., A novel peptide, THALWHT, for the targeting of human airway epithelia. FEBS Lett. Feb. 2, 2001;489(2-3):263-9.

Kawana et al., In vitro construction of pseudovirions of human papillomavirus type 16: incorporation of plasmid DNA into reassembled L1/L2 capsids. J Virol. Dec. 1998;72(12):10298-300.

Kines et al., An Infrared Dye-Conjugated Virus-like Particle for the Treatment of Primary Uveal Melanoma. Mol Cancer Ther. Feb. 2018;17(2):565-574. doi: 10.1158/1535-7163.MCT-17-0953. Epub Dec. 14, 2017.

Kines et al., Human papillomavirus capsids preferentially bind and infect tumor cells. Int J Cancer. Feb. 15, 2016;138(4):901-11. doi: 10.1002/ijc.29823. Epub Oct. 27, 2015.

Kirnbauer et al. Efficient self-assembly of human papillomavirus type 16 L1 and L1-L2 into virus-like particles. Journal of virology. Dec. 1, 1993;67(12):6929-36.

Kirnbauer et al. Papillomavirus L1 major capsid protein self-assembles into virus-like particles that are highly immunogenic. Proceedings of the National Academy of Sciences. Dec. 15, 1992;89(24):12180-4.

Lavelle et al., The disassembly, reassembly and stability of CCMV protein capsids. J Virol Methods. Dec. 2007; 146(1-2):311-6. Epub Sep. 4, 2007.

Lee et al., Adaptations of nanoscale viruses and other protein cages for medical applications. Nanomedicine. Sep. 2006;2(3):137-49.

Leong et al., Intravital imaging of embryonic and tumor neovasculature using viral nanoparticles. Nat Protoc. Aug. 2010;5(8):1406-17. doi: 10.1038/nprot.2010.103. Epub Jul. 8, 2010.

Li et al, Expression of the human papillomavirus type 11 LI capsid protein in Escherichia coli: characterization of protein domains involved in DNA binding and capsid assembly. J Viral. Apr. 1997;71(4):2988-95.

Li et al, Trackable and Targeted Phage as Positron Emission Tomography (PET) Agent for Cancer Imaging. Theranostics. 2011;1:371-80. Epub Nov. 18, 2011.

Lin et al., Treatment of established tumors with a novel vaccine that enhances major histocompatibility class II presentation of tumor antigen. Cancer Res. Jan. 1, 1996;56(1):21-6.

(56) References Cited

OTHER PUBLICATIONS

Melero et al., Evolving synergistic combinations of targeted immunotherapies to combat cancer. Nat Rev Cancer. Aug. 2015;15(8):457-72. doi: 10.1038/nrc3973.

Mitsunaga et al., In vivo longitudinal imaging of experimental human papillomavirus infection in mice with a multicolor fluorescence mini-endoscopy system. Cancer Prev Res (Phila). May 2011;4(5):767-73. doi: 10.1158/1940-6207.CAPR-10-0334. Epub Mar. 23, 2011.

Oh et al., Enhanced mucosal and systemic immunogenicity of human papillomavirus-like particles encapsidating interleukin-2 gene adjuvant. Virology. Oct. 25, 2004;328(2):266-73.

Pedersen et al. Immunization of early adolescent females with human papillomavirus type 16 and 18 L1 virus-like particle vaccine containing AS04 adjuvant. Journal of Adolescent Health. Jun. 30, 2007;40(6):564-71.

Peng et al., Construction and production of fluorescent papillomavirus-like particles. J Tongji Med Univ. 1999;19(3):170-4, 180.

Pinto et al. Cellular immune responses to human papillomavirus (HPV)-16 L1 in healthy volunteers immunized with recombinant HPV-16 L1 virus-like particles. Journal of Infectious Diseases. Jul. 15, 2003;188(2):327-38.

Pyeon et al., Production of infectious human papillomavirus independently of viral replication and epithelial cell differentiation. Proc Natl Acad Sci U S A. Jun. 28, 2005;102(26):9311-6. Epub Jun. 15, 2005.

Raja et al., Hybrid virus-polymer materials. 1. Synthesis and properties of PEG-decorated cowpea mosaic virus. Biomacromolecules. May-Jun. 2003;4(3):472-6.

Rhee et al., Glycan-targeted virus-like nanoparticles for photodynamic therapy. Biomacromolecules. Aug. 13, 2012;13(8):2333-8. doi: 10.1021/bm300578p. Epub Jul. 24, 2012. Author manuscript.

Rose et al. Expression of human papillomavirus type 11 L1 protein in insect cells: in vivo and in vitro assembly of viruslike particles. Journal of Virology. Apr. 1, 1993;67(4):1936-44.

Rudolf et al., Human dendritic cells are activated by chimeric human papillomavirus type-16 virus-like particles and induce epitope-specific human T cell responses in vitro. J Immunol. May 15, 2001;166(10):5917-24.

Ruehlmann et al., MIG (CXCL9) chemokine gene therapy combines with antibody-cytokine fusion protein to suppress growth and dissemination of murine colon carcinoma. Cancer Res. Dec. 1, 2001;61(23):8498-503.

Ryding et al., Deletion of a major neutralizing epitope of human papillomavirus type 16 virus-like particles. J Gen Virol. Mar. 2007;88(Pt 3):792-802.

Sadeyen et al., Insertion of a foreign sequence on capsid surface loops of human papillomavirus type 16 virus-like particles reduces their capacity to induce neutralizing antibodies and delineates a conformational neutralizing epitope. Virology. Apr. 25, 2003;309(1):32-40.

Schädlich et al., Refining HPV 16 L1 purification from *E. coli*: reducing endotoxin contaminations and their impact on immunogenicity. Vaccine. Mar. 4, 2009;27(10):1511-22. Epub Jan. 25, 2009.

Singh, Tumor targeting using canine parvovirus nanoparticles. Curr Top Microbiol Immunol. 2009;327:123-41.

Speir et al., Structures of the native and swollen forms of cowpea chlorotic mottle virus determined by X-ray crystallography and cryo-electron microscopy. Structure. Jan. 15, 1995;3(1):63-78.

Stephanopoulos et al., Dual-surface modified virus capsids for targeted delivery of photodynamic agents to cancer cells. ACS Nano. Oct. 26, 2010;4(10):6014-20. doi: 10.1021/nn1014769.

Touze et al., In vitro gene transfer using human papillomavirus-like particles. Nucleic Acids Res. Mar. 1, 1998;26(5):1317-23.

Touze et al., The L1 major capsid protein of human papillomavirus type 16 variants affects yield of virus-like particles produced in an insect cell expression system. J Clin Microbiol. Jul. 1998;36(7):2046-51.

Touzé et al., The nine C-terminal amino acids of the major capsid protein of the human papillomavirus type 16 are essential for DNA binding and gene transfer capacity. FEMS Microbiol Lett. Aug. 1, 2000;189(1):121-7.

Uchida et al., Biological Containers: Protein Cages as Multifunctional Nanoplatforms. Adv Mater. 2007;19:1025-42.

Varsani et al., Chimeric human papillomavirus type 16 (HPV-16) L1 particles presenting the common neutralizing epitope for the L2 minor capsid protein of HPV-6 and HPV-16. J Virol. Aug. 2003;77(15):8386-93.

Vaysse et al., Improved transfection using epithelial cell line-selected ligands and fusogenic peptides. Biochim Biophys Acta. Jul. 26, 2000;1475(3):369-76.

Wang et al., Insertion of a targeting peptide on capsid surface loops of human papillomavirus type-16 virus-like particles mediate elimination of anti-dsDNA Abs-producing B cells with high efficiency. J Immunother. Jan. 2009;32(1):36-41.

Wang et al., Expression of Human Papillomavirus Type 6 L1 and L2 Isolated in China and Self Assembly of Virus-like Particles by the Products. Acta Biochimica et Biophysica Sinica. 2003;35(1):27-34. 10 pages.

Wang et al., Human papillomavirus type 6 virus-like particles present overlapping yet distinct conformational epitopes. J Gen Virol. Jun. 2003;84(Pt 6):1493-7.

White et al., Genetic modification of adeno-associated viral vector type 2 capsid enhances gene transfer efficiency in polarized human airway epithelial cells. Hum Gene Ther. Dec. 2008;19(12):1407-14.

Willits et al., Effects of the cowpea chlorotic mottle bromovirus beta-hexamer structure on virion assembly. Virology. Feb. 15, 2003;306(2):280-8.

Xu et al., Papillomavirus virus-like particles as vehicles for the delivery of epitopes or genes. Arch Virol. Nov. 2006;151(11):2133-48. Epub Jun. 22, 2006.

Yoshinouchi et al., In vitro and in vivo growth suppression of human papillomavirus 16-positive cervical cancer cells by E6 siRNA. Mol Ther. Nov. 2003;8(5):762-8.

Zhang et al. Expression of Human Papillomavirus Type 16 L1 Protein in *Escherichia coli*: Denaturation, Renaturation, and Self-Assembly of Virus-like Particlesin Vitro. Virology. Apr. 10, 1998;243(2):423-31.

Zhou et al. Expression of vaccinia recombinant HPV 16 L1 and L2 ORF proteins in epithelial cells is sufficient for assembly of HPV virion-like particles. Virology. Nov. 1, 1991;185(1):251-7.

U.S. Appl. No. 13/264,213, filed Mar. 2, 2012, Coursaget et al., Granted.

U.S. Appl. No. 15/636,112, filed Jun. 28, 2017, Coursaget et al., Granted.

U.S. Appl. No. 16/204,019, filed Nov. 29, 2018, Coursaget et al., Published.

U.S. Appl. No. 14/376,408, filed Aug. 1, 2014, de los Pinos et al., Granted.

U.S. Appl. No. 15/615,485, filed Jun. 6, 2017, de los Pinos et al., Granted.

U.S. Appl. No. 15/824,685, filed Nov. 28, 2017, de los Pinos et al., Granted.

U.S. Appl. No. 16/376,435, filed Apr. 5, 2019, de los Pinos et al., Allowed.

U.S. Appl. No. 15/023,169, filed Mar. 18, 2016, de los Pinos et al., Granted.

U.S. Appl. No. 16/143,147, filed Sep. 26, 2018, de los Pinos et al., Allowed.

U.S. Appl. No. 15/772,134, filed Apr. 30, 2018, Lobb et al., Published.

PCT/IB2010/002654, Aug. 8, 2011, International Preliminary Report on Patentability.

PCT/US2018/027080, Jun. 28, 2018, International Search Report and Written Opinion.

PCT/US2018/027080, Oct. 24, 2019, International Preliminary Report on Patentability.

* cited by examiner

METHODS FOR TREATING BLADDER TUMORS WITH VIRAL NANOPARTICLE CONJUGATES AND IMMUNE CHECKPOINT INHIBITORS

RELATED APPLICATIONS

This application is a national stage filing under 35 U.S.C. § 371 of international application number PCT/US2018/027080, filed Apr. 11, 2018, which was published under PCT Article 21(2) in English and claims the benefit under 35 U.S.C. § 119 (e) of U.S. provisional application No. 62/484,693, filed Apr. 12, 2017, each of which is incorporated by reference herein in its entirety.

BACKGROUND

Although numerous treatments are available for cancer, many forms of cancer remain incurable, untreatable or become resistant to standard therapies. Traditional cancer treatment methods are frequently accompanied by severe side effects, due to the cytotoxicity caused in normal/healthy cells by the anti-cancer drugs.

SUMMARY

The present disclosure provides methods and compositions for selectively targeting and killing tumor cells while simultaneously presenting tumor antigens to the immune system and synergistically generating anti-tumor immunity, thereby providing a combination therapy for the treatment and prevention of cancer. Unexpectedly, experimental data has shown that tumor-targeted photosensitive molecules, which become cytotoxic upon laser activation, trigger a tumor antigen-specific immune response. To boost this immune response against the cancer cells, immune checkpoint inhibitors may be administered concurrently (or sequentially) with the tumor-targeted photosensitive molecules.

Thus, in some embodiments, provided herein are methods that include (a) administering, to a subject having a tumor, a composition comprising tumor-targeting viral capsid protein assemblage that comprises photosensitive molecules conjugated to viral capsid proteins of the assemblage; and (b) administering to the subject having a tumor, a composition comprising an immune checkpoint inhibitor.

In some embodiments, an immune checkpoint inhibitor is administered to a subject having a tumor who is undergoing treatment with a tumor-targeting viral capsid protein assemblage that comprises photosensitive molecules conjugated to viral capsid proteins of the assemblage.

Also provided herein are compositions that include an immune checkpoint inhibitor and a tumor-targeting viral capsid protein assemblage that comprises photosensitive molecules conjugated to viral capsid proteins of the assemblage.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

DETAILED DESCRIPTION

Figure 1:
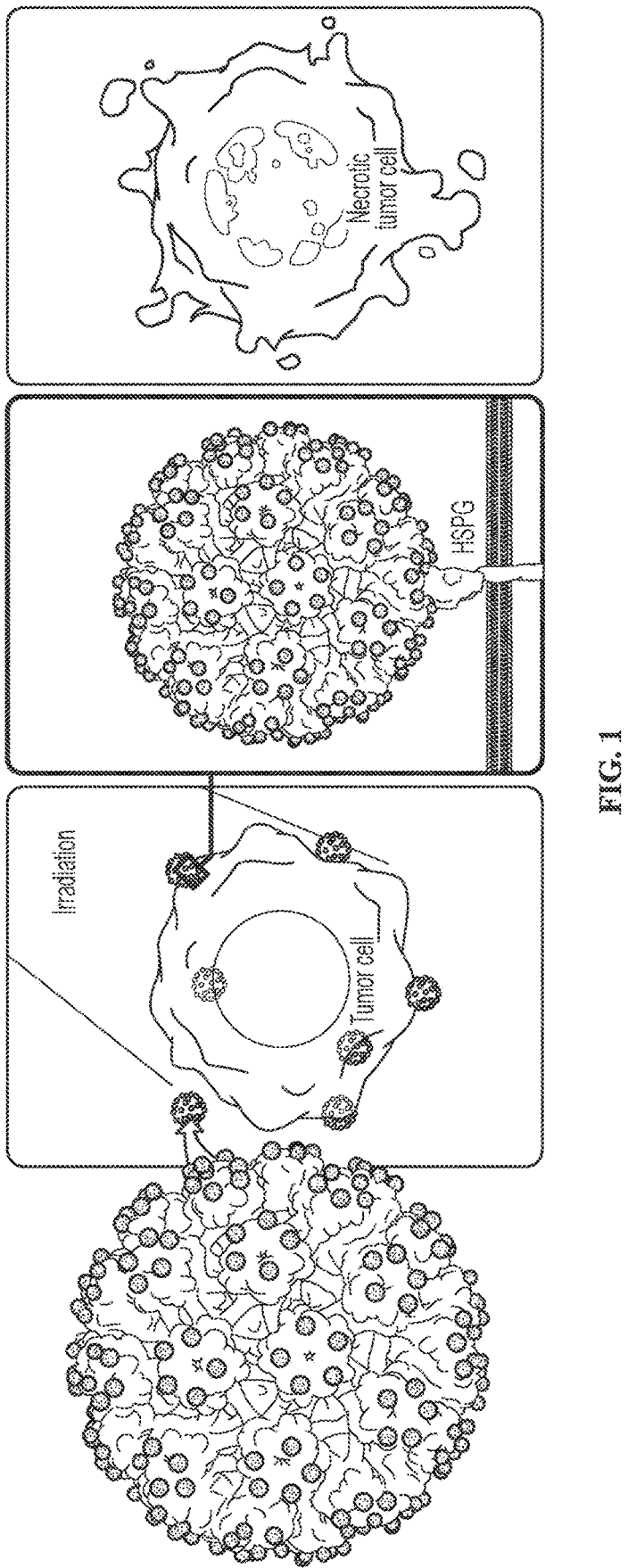
FIG. 1 is a schematic depicting the mechanism of action of a VLP conjugate of the present disclosure, which include a tumor-targeting virus-like particle (VLP) having photosensitive molecules (IRDye®700DX) conjugated to the primary amines in the surface of the VLP. The VLP conjugate is inactive without irradiation. VLP conjugates preferentially target tumor cells. Infrared irradiation, at 689 nm, activates the VLP conjugate. L1 proteins of the viral capsid bind specifically to heparan sulfate proteoglycans (HSPGs) on the tumor surface in a multivalent manner. The activated drug then disrupts the tumor cell membrane, leading to pro-immunogenic tumor cell damage and necrosis.

To deliver cancer/tumor treatment drugs specifically to a tumor, certain viral capsid proteins can be assembled and/or chemically modified to carry therapeutic molecules without losing their tumor-targeting capability or structural stability. These "viral capsid protein assemblages" can selectively bind to a tumor cell surface, e.g., via binding to heparan sulphate proteoglycans (HSPGs) on tumor cell surface, and enter the tumor cell, where the therapeutic molecule (e.g., photosensitive molecule) can generate targeted cytotoxic effects and/or anti-tumor immunity, leading to tumor cell death and prevention of tumor recurrence. The use of such virus-like particles and assemblages in treating cancer, has been described, e.g., in PCT Application Publication WO2015042325, filed Sep. 18, 2014, the entirety of which is herein incorporated by reference.

Some aspects of the present disclosure are based, at least in part, on unexpected results demonstrating that photosensitive molecules delivered to tumor cells via tumor-targeting viral capsid protein assemblages generate anti-tumor immunity. Tumor cells that undergo pro-immunogenic cell death release immunogenic factors that stimulate antigen presenting cells (APCs) to take up the tumor antigens, process them, and induce tumor antigen-specific T-cell immune responses against the tumor. Such tumor antigen-specific T-cell responses, combined with the necrotic effects of treatment, presents immense potential for selectively and effectively destroying tumor cells, without affecting normal cells, generating anti-tumor immunity and preventing tumor recurrence.

Tumor cells frequently exploit the mechanisms adopted by the immune system to prevent self-attacking. Cancer immunotherapeutic agents have been developed to reduce or eliminate the ability of tumor cells to evade being attacked by the immune system. The use of such immunotherapeutic agents to treat cancer have been described, e.g., in US Patent Application Publication US20160024469, US20130202645, US20100189641, U.S. Pat. Nos. 5,478,556, 5,290,551, and 5,126,129, the entirety of which are incorporated by reference herein. In some embodiments, the immunotherapeutic agent is an immune checkpoint inhibitor. Thus, the present disclosure encompasses compositions and methods for combination therapy of cancer/tumors, utilizing an unexpected synergistic effect produced by targeting and activating cytotoxic photosensitive molecules in tumor cells and concurrently or sequentially administering an immune checkpoint inhibitor (or other immunotherapeutic agent). Such compositions and methods are more effective in controlling tumor growth, inducing antitumor immunity, and preventing tumor recurrence when compared to traditional chemotherapeutic methods and tumor immunotherapy strategies.

Accordingly, some aspects of the present disclosure provide compositions comprising tumor-targeting viral capsid protein assemblage that comprises photosensitive molecules conjugated to viral capsid proteins of the assemblage.

A "viral capsid protein assemblage" is any particle or aggregate formed from viral capsid proteins. Examples of viral capsid protein assemblages include, without limitation, capsomeres and virus-like nanoparticles, and other viral pseudoviruses and viral nanoparticles. A viral capsid protein assemblage is considered "tumor targeting" because it binds tumor (e.g., cancerous) cells without binding non-tumor (e.g., non-cancerous, otherwise normal, healthy) cells. In some embodiments, a tumor-targeting viral capsid protein assemblage is a virus-like particle (VLP) having a 72-capsomere structure (e.g., comprising L1 or L1/L2 viral capsid proteins).

In some embodiments, a viral capsid protein assemblage is a human papillomavirus viral (HPV) capsid protein assemblage (e.g., from type 16, type 31 or a modified type that includes amino acids from type 16 and amino acids from type 31). In some embodiments, a viral capsid protein assemblage is a non-human papillomavirus viral (HPV) capsid protein assemblage. Examples of non-human papillomavirus viral capsid protein assemblages include, but are not limited to, bovine papillomaviruses, cotton-rabbit papillomaviruses, macaque papillomaviruses and murine papillomaviruses.

A viral capsid protein assemblage comprises viral capsid proteins. A "capsid protein" is a protein monomer. Capsid proteins can assemble together to form a capsomere (e.g., a pentamer of capsid proteins). A "capsomere" is a subunit of a viral capsid, which is an outer covering of protein that protects the genetic material of a virus such as, for example, human papillomavirus (HPV). It should be understood, however, the capsomeres in the context of the present disclosure may be used as delivery vehicles (tumor-targeting delivery vehicles), independent of a capsid. The capsid proteins of the present disclosure include papillomavirus L1 capsid proteins, papillomavirus L2 capsid proteins, and variants thereof (e.g., variants having reduced or modified ability to induce infection inhibiting antibodies). In some embodiments, a viral capsid protein assemblage includes only L1 capsid proteins, while in other embodiments, a viral capsid protein assemblage includes a combination of L1 and L2 capsid proteins. An "external capsid protein," as used herein, refers to a capsid protein that is exposed on the surface of a VLP.

A virus-like particle, or VLP, as used herein, refers to an organized capsid-like structure (e.g., roughly spherical or cylindrical in shape) that comprises self-assembling ordered arrays of L1, or L1 and L2, capsomeres and does not include a viral genome. In some embodiments, the virus-like particles are morphologically and antigenically similar to authentic virions, but they lack viral genetic material (e.g., viral nucleic acid), rendering the particles non-infectious.

Tumor-targeting viral capsid protein assemblage may be modified, in some embodiments, to reduce immunogenicity against the particle itself, i.e., to reduce the induction of neutralizing antibodies against the assemblages. The viral capsid protein assemblages may, for example, be assembled from capsomeres having a variant capsid protein with modified immunogenicity. A variant capsid protein with "modified immunogenicity" is one that is modified naturally or synthetically (e.g., mutated, substituted, deleted, PEGylated or inserted) at an amino acid to reduce or prevent recognition of the capsid protein by pre-existing (e.g., endogenous) viral serotype-specific antibodies. A variant capsid protein may be a human papillomavirus (HPV) L1 variant, a non-human papillomavirus L1 variant, or a papillomavirus L1 variant based on a combination of amino acids from different HPV serotypes. For example, an L1 variant with modified immunogenicity may be a recombinant protein, which is described in International Pub. No. WO2010120266, filed Jul. 24, 2009, the entirety of which is incorporated by reference herein. In some embodiments, the viral capsid protein assemblages comprise L1 variants with modified immunogenicity (variant HPV16/31 L1 capsid proteins).

The tumor-targeting viral capsid protein assemblages of the present disclosure can specifically target cancer cells and such specificity is mediated, at least in part, by the binding of L1 protein in the viral capsid protein assemblage to heparan sulfate proteoglycans (HSPGs) on the tumor cell surface. This process is analogous to the process of a virus attaching and infecting its host cells. The tumor-targeting viral capsid protein assemblages do not bind to or pseudo-target intact epithelial cells, and thus are excellent tools for delivering anti-cancer drugs specifically to tumors without affecting the healthy or normal cells.

The tumor-targeting viral capsid protein assemblages of the present disclosure, comprise capsid proteins conjugated to molecules that have anti-cancer activities, herein referred to as "anti-cancer molecules." Such anti-cancer molecules are capable of generating a targeted cytotoxic effect on tumor cells and/or can in some instances induce immunity against the tumor cells. Non-limiting examples of the molecules of the present disclosure include bortezomib, imatinib, seliciclib, Afatinib (Gilotrif), Alectinib (Alecensa), Axitinib (Inlyta), Belinostat (Beleodaq), Bortezomib (Velcade), Bosutinib (Bosulif), Cabozantinib (Cometriq), Carfilzomib (Kyprolis), Ceritinib (Zykadia), Cobimetinib (Cotellic), Crizotinib (Xalkori), Dabrafenib (Tafinlar), Dasatinib (Sprycel), Erlotinib (Tarceva), Everolimus (Afinitor), Gefitinib (Iressa), Ibrutinib (Imbruvica), Idelalisib (Zydelig), Imatinib (Gleevec), Ixazomib (Ninlaro), Lapatinib (Tykerb), Lenvatinib (Lenvima), Nilotinib (Tasigna), Olaparib (Lynparza), Osimertinib (Tagrisso), Palbociclib (Ibrance), Panobinostat (Farydak), Pazopanib (Votrient), Ponatinib (Iclusig), Regorafenib (Stivarga), Ruxolitinib (Jakafi), Sipuleucel-T (Provenge), Sonidegib (Odomzo), Sorafenib (Nexavar), Temsirolimus (Torisel), Tofacitinib (Xeljanz), Trametinib (Mekinist), Vandetanib (Caprelsa), Vemurafenib (Zelboraf), Vismodegib (Erivedge), and Vorinostat (Zolinza). Any anti-cancer molecule known in the art may be used in accordance with the present disclosure.

In some embodiments, the anti-cancer molecule is a photosensitive molecule, or a photosensitizer. A "photosensitive molecule" or "photosensitizer" is a chemical compound that can be promoted to an excited state upon absorption light. This species rapidly attacks any organic compounds it encounters, thus being highly cytotoxic. In some embodiments, an activated photosensitive molecule re-emits light upon light excitation (e.g., a fluorophore). In some embodiments, an activated photosensitive molecule can become toxic, or can produce toxic molecules, upon light excitation. For example, a class of photosensitive molecules can be promoted to an excited state upon absorption of light and undergo intersystem crossing with oxygen to produce singlet oxygen.

Surprisingly, tumor-targeting viral capsid protein assemblages comprising photosensitive molecules conjugated to viral capsid proteins once activated with NIR light not only induced tumor necrosis, but also induced pro-immunogenic cell death of the tumor and activated long lasting tumor antigen-specific T-cell response against the tumor. As such, the immune system is activated to attack the tumor, enhancing the local (regional) and distant treatment efficacy. Unexpectedly, this mechanism of action not only reduced the size of the existing tumor, i.e., inhibited tumor growth, but also prevented new tumor from forming upon challenge in mice, i.e., prevented tumor recurrence.

Examples of photosensitive molecules for use in accordance with the present disclosure include, but are not limited to, fluorescent dyes, infrared dyes, near infrared dyes, porphyrin molecules and chlorophyll molecules.

Examples of fluorescent dyes for use in accordance with the present disclosure include, without limitation, acridine orange, acridine yellow, Alexa Fluor, 7-Aminoactinomycin D, 8-Anilinonaphthalene-1-sulfonic acid, ATTO dyes, auramine-rhodamine stain, benzanthrone, bimane, 9,10-Bis (phenylethynyl)anthracene, 5,12-Bis(phenylethynyl)naphthacene, bisbenzimide, blacklight paint, calcein, carboxyfluorescein, carboxyfluorescein diacetate succinimidyl ester, carboxyfluorescein succinimidyl ester, 1-chloro-9,10-bis(phenylethynyl)anthracene, 2-chloro-9,10-bis(phenylethynyl)anthracene, 2-chloro-9,10-diphenylanthracene, coumarin, DAPI, dark quencher, DiOC6, DyLight Fluor, Fluo-3, Fluo-4, FluoProbes, fluorescein, fluorescein isothiocyanate, fluorescence image-guided surgery, fluorojade stain, fura-2, fura-2-acetoxymethyl ester, GelGreen, GelRed, green fluorescent protein, heptamethine dyes, Indian yellow, Indo-1, Lucifer yellow, luciferin, MCherry, Merocyanine, Nile blue, Nile red, optical brightener, perylene, phloxine, phycobilin, phycoerythrin, phycoerythrobilin, propidium iodide, pyranine, rhodamine, rhodamine 123, Rhodamine 6G, RiboGreen, RoGFP, Rose Bengal, rubrene, (E)-stilbene, (Z)-stilbene, sulforhodamine 101, sulforhodamine B, SYBR Green I, synapto-pHluorin, tetraphenyl butadiene, tetrasodium tris(bathophenanthroline disulfonate)ruthenium(II), Texas Red, Titan yellow, TSQ, umbelliferone, yellow fluorescent protein and YOYO-1.

Examples of photosensitizing dyes for use in accordance with the present disclosure include, without limitation, HpD, Porfimer sodium(Photofrin®, Photogem®, Photosan Hemporfin®), m-THPC, Temoporfin (Foscan®), Verteporfin (Visudyne®), HPPH (Photochlor®), Palladium-bacteria-pheophorbide (Tookad®,) 5-ALA, 5 aminolevulinic acid (Levulan®), 5-ALA methylester (Metvix®), 5-ALA benzylester (Benzvix®), 5-ALA hexylester (Hexvix®), lutetium (III)-texaphyrin or Motexafin-lutetium (Lutex®, Lutrin®, Angrin®, Optrin®), SnET2, Tin (IV) ethyl etiopurpurin (Purlytin®, Photrex®), NPe6, mono-L-aspartyl chlorine e6, talaporfin sodium (Talporfin®, Laserphyrin®), BOPP, boronated protoporphyrin (BOPP®), Zinc phthalocyanine (CGP55847®), silicon phthalocyanine (Pc4®), mixture of sulfonated aluminium phthalocyanine derivatives (Photosens®), ATMPn, Acetoxy-tetrakis (beta-methoxyethyl-)porphycene), TH9402 and dibromorhodamine methyl ester.

Examples of photosensitizing molecules for use in accordance with the present disclosure include those that can be used in fluorescence imaging (e.g., near infrared (NIR) fluorescent dyes) such as porphyrin, chlorophyll, chlorin, phthalocyanine, bacteriochlorin, texaphyrin, Photofrin® (porfimer sodium), Visudyne® (verteporfin), Laserphyrin®/NPe6 (temoporfin), Foscan (talaporfin), Methylene Blue (Urolene Blue®, Swiss Blue, Basic Blue 9, Chromosmon, Methylthionium Chloride), and various derivatives of amino levulinic acid (ALA, Metvix®, Hexvix™/Cysview®), or a combination thereof. In some embodiments, the photosensitizing molecule conjugated to the viral capsid protein assemblage of the present disclosure is a near infrared dye. In some embodiments, the near-infrared dye is IRDye®700DX.

In accordance with various aspects of the present disclosure, the anti-cancer molecules (e.g., IRDye® 700DX) may be conjugated to capsid proteins (e.g., papillomavirus L1 and/or L2 capsid proteins) of the viral capsid protein assemblages. In some embodiments, the anti-cancer molecules are covalently conjugated to capsid proteins of the viral capsid protein assemblages. In some embodiments, the anti-cancer small molecules are covalently conjugated to lysine residues of capsid proteins of the viral capsid protein assemblages. Conjugating the anti-cancer molecules to the capsid proteins does not compromise the binding of the viral capsid protein assemblages to the surface of tumor cells, or compromise the binding of the viral capsid protein assemblages to HSPGs on the surface of tumor cells. Viral capsid protein assemblages that are conjugated to the anti-cancer molecules may be referred to herein as "conjugates."

The L1 protein of the papilloma virus contains a high number of lysines that are accessible to chemical conjugations. Therefore, a large number of photosensitive molecules (or other anti-cancer molecules) may be conjugated to one tumor-targeting viral capsid protein assemblage of the present disclosure, i.e., the ratio of anti-cancer molecules to viral capsid protein assemblage may vary. In some embodiments the ratio of viral capsid protein assemblage:photosensitive molecule is about 1:10 to about 1:1000, or about 1:50 to about 1:1000. That it, in some embodiments, a viral capsid protein assemblage may comprise about 10 to about 1000 photosensitive molecules. In some embodiments, the ratio of viral capsid protein assemblage:photosensitive molecule is 1:10, 1:15, 1:20, 1:25, 1:50, 1:75, 1:100, 1:150, 1:200, 1:250, 1:500, 1:750 or 1:1000. In some embodiments, the viral capsid protein assemblage may comprise 10, 15, 20, 50, 75, 100, 150, 200, 250, 300, 350, 400, 450, 500, 550, 600, 650, 700, 750, 800, 850, 900, 950, or 1000 photosensitive molecules. For example, the viral capsid protein assemblage may comprise 10 to 1000, 10 to 500, 100 to 1000, 200 to 1000, 300 to 1000, 400 to 1000, 500 to 1000, 100 to 500, 200 to 500, 300 to 500, 400 to 500, 100 to 400, 200 to 400, 300 to 400, 100 to 300, or 200 to 300 photosensitive molecules. In some embodiments, the viral capsid protein assemblage may comprise more than 1000 photosensitive molecules or less than 10 anti-cancer molecules. Conjugating photosensitive molecules to the L1 protein of the viral capsid protein assemblage does not comprise the structural integrity or tumor-targeting capability of the assemblage, i.e., its ability to selectively bind the HSPGs on the surface of the tumor cells. Thus, another advantage of the tumor-targeting viral capsid protein assemblages of the present disclosure are their capability to deliver high amounts of therapeutic agents specifically to the tumor even at a very low concentration of the molecule.

In some embodiments, the tumor-targeting viral capsid protein assemblage comprises a photosensitive molecule conjugated to the viral capsid proteins. In some embodiments, the photosensitive molecule is IRDye®700DX. In some embodiments, the viral particle conjugate includes a virus-like particle, e.g., a virus-like particle comprising 72 capsomeres assembled from variant or modified HPV 16/31 L1 capsid proteins and wild-type HPV L2 capsid proteins, conjugated to an infra-red activated molecule, e.g., IRDye®700DX. This conjugate has been shown to bind selectively to cancer cells and upon activation with a laser, the conjugate selectively destroys the membrane of cancer cells, killing them without damaging the neighboring normal cells.

The composition of the present disclosure further comprises an immunotherapeutic agent for the treatment of cancer. An "immunotherapeutic agent", as used herein, refers to agents that promote the use of the immune system to treat cancer. Such immunotherapeutic agents typically exploit the fact that cancer cells often have molecules on their surface that can be detected by the immune system. In some embodiments, the immunotherapeutic agents actively directs the immune system to attach tumor cells. In some embodiments, the immunotherapeutic agents enhance existing anti-tumor responses, e.g., monoclonal antibodies, lymphocytes, and cytokines.

In some embodiments, the immunotherapeutic agents modulate the activities of immune checkpoints.

"Immune checkpoints" are proteins in the immune system that either enhance an immune response signal (co-stimulatory molecules) or reduce an immune response signal. Many cancers protect themselves from the immune system by exploiting the inhibitory immune checkpoint proteins to inhibit the T cell signal. Such inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GAL9), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3) and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reduces the immune response.

Cancer cells are known to exploit the immune checkpoint proteins to escape being attacked by the immune system. Therefore, the use of immune checkpoint inhibitors to enhance an immune response against cancer, and thus treating cancer, have been described. The immunotherapeutic agents in the compositions of the present disclosure may also be immune checkpoint inhibitors. In some embodiments, the immune checkpoint inhibits any one or more of Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GAL9), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3) and V-domain Ig suppressor of T cell activation (VISTA).

In some embodiments, "inhibit" means preventing or weakening the binding of the immune checkpoint protein to its cognate binding partner, e.g., PD-1, CTLA-4, or A2aR. In some embodiments, the immune checkpoint inhibitor is an antibody. In some embodiments, the antibody comprises an anti-CTLA-4, anti-PD-1, anti-PD-L1, anti-TIM3, anti-LAG3, anti-B7-H3, anti-B7-H4, anti-BTLA, anti-GALS, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (Keytruda®) or nivolumab (Opdivo®) and the anti-CTLA-4 antibody is ipilimumab (Yervoy®). Thus, in some embodiments, the immune checkpoint inhibitor comprises pembrolizumab, nivolumab, ipilimumab, or any combination of two or more of the foregoing antibodies. It is to be understood that the examples described herein are not meant to be limiting and that any immune checkpoint inhibitors known in the art and any combinations thereof may be used in accordance with the present disclosure.

The compositions comprising tumor-targeting viral capsid protein assemblages and immunotherapeutic agents disclosed herein are suitable for treatment of cancer. Thus, the present disclosure also encompasses methods of administering to a subject having a tumor such compositions to treat the tumor. The composition is administered to the subject in an amount effective to reduce tumor growth and/or prevent recurrence of the tumor.

"Administering" or "administration" or "administer" means providing a material to a subject in a manner that is pharmacologically useful. Conventional methods, known to those of ordinary skill in the art of medicine, can be used to administer the therapeutic agent or composition to the subject, depending upon the type of cancer to be treated or the site of the cancer. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intra-bladder, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some embodiments, the composition may be administered systemically, e.g., intravenously. In some embodiments, the composition is administered topically. In some embodiments, the composition is administered by implantation.

In some embodiments, the compositions of the present disclosure may be injected to a target site where tumor growth is present. Injection methods that may be used in accordance with the present disclosure include, without limitation, intravenous injection, intralesional injection, subcutaneous injection, intravitreal injection, suprachoroidal injection, intraperitoneal injection, intra-arterial injection, intra-hepatic injection and intravesical injection. In the instances where injections are used, hollow needles, coated needles, mini-needles or micro-needles are used, depending on the area of injection.

In some embodiments, the cancer treatment methods of the present disclosure comprise administering to a subject having a tumor, a composition comprising tumor-targeting viral capsid protein assemblages that comprises photosensitive molecules conjugated to viral capsid proteins and a composition comprising an immunotherapeutic agent.

In some embodiments, the tumor-targeting viral capsid protein assemblage and the immunotherapeutic agent are administered concurrently. "Concurrently" means administering two or more materials/agents (e.g., the tumor-targeting viral capsid protein assemblage and the immunotherapeutic agent) to a subject at the same time. For example, the compositions comprising the tumor-targeting viral capsid protein assemblage or the immunotherapeutic agent may be combined/mixed before administration.

In some embodiments, the tumor-targeting viral capsid protein assemblage and the immunotherapeutic agent are administered sequentially. "Sequentially" means the administering of one agent and the administering of another agent are separated in time (in two separate steps). In some embodiments, the tumor-targeting viral capsid protein assemblage is administered first and the immunotherapeutic agent (e.g., checkpoint inhibitor) is administered second. In some embodiments the immunotherapeutic agent is administered first and the tumor-targeting viral capsid protein assemblage is administered second. The time between the two steps of administering steps may be at least 1 minute, at least 5 minutes, at least 30 minutes, at least 1 hour, at least 5 hours, at least 10 hours, at least 1 day, at least 1 week, or even at least one month. When the tumor-targeting viral capsid protein assemblage and the immunotherapeutic agent are administered sequentially, they may also be administered via different routes or to different locations. For example, the tumor-targeting viral capsid protein assemblage may be administered intralesionally to the exposed tumor lesion or subcutaneously to the cutaneous of the subject, while the immunotherapeutic agent may be administered systemically, e.g., intravenously.

In some embodiments, the cancer treatment methods of the present disclosure comprises administering an immunotherapeutic agent to a subject having a tumor who is undergoing treatment with a tumor-targeting viral capsid protein assemblage that comprises molecules (e.g. photosensitive molecules) conjugated to viral capsid proteins.

Photosensitive molecules of the present disclosure, depending on the type of molecule, can be activated by infrared, near-infrared or ultraviolet light. For example, an infrared, near-infrared or ultraviolet laser may be used, in some embodiments, to activate the photosensitive molecules of the tumor-targeting viral capsid protein assemblage. The energy delivered by the laser may range from 5 Joules (J) to about 150 J, or 8 J to 36 J. In some embodiments, the energy delivered by the laser is 5 J, 6 J, 7 J, 8 J, 9 J, 10 J, 12 J, 14 J, 16J, 18 J, 20 J, 22 J, 24 J, 26 J, 28 J, 30 J, 32 J, 34 J, 36 J, 38 J, 40 J, 50 J, 60 J, 70 J, 80 J, 90 J, 100 J, 110 J, 120 J, 130 J, 140 J, or 150 J.

A light or laser may be applied to the photosensitive molecules (or the tumor-targeting viral capsid protein assemblage) from about 5 seconds to about 5 minutes. For example, in some embodiments, the light or laser is applied to the photosensitive molecules for 5, 10, 15, 20, 25, 30, 35, 40, 45 50 or 55 seconds to activate the molecules. In some embodiments, the laser is applied to the photosensitive molecules for 1, 1.5, 2, 2.5, 3, 3.5, 4, 4.5 or 5 minutes.

A light or laser may be applied to the photosensitive molecules (or the tumor-targeting viral capsid protein assemblage) about 30 minutes to about 48 hours after administering the tumor-targeting viral capsid protein assemblage. For example, in some embodiments, the light or laser is applied to the photosensitive molecules 30, 35, 40, 45, 50 or 55 minutes after administering the tumor-targeting viral capsid protein assemblage. In some embodiments, the light or laser is applied to the photosensitive molecules 1, 2, 3, 4, 5, 6, 7, 8, 9, 10, 11, 12, 13, 14, 15, 16, 17, 18, 19, 20, 21, 22, 23, or 24 hours after administering the tumor-targeting viral capsid protein assemblage. In some embodiments, the light or laser is applied to the photosensitive molecules 36 or 48 hours after administering the tumor-targeting viral capsid protein assemblage.

The light or laser may be applied directly to the site of the tumor, for example.

According to the cancer treatment methods of the present disclosure, a subject having a tumor who is undergoing treatment with a viral capsid protein assemblage conjugated to photosensitive molecules may be further administered an immunotherapeutic agent, e.g., an immune checkpoint inhibitor. Any immunotherapeutic agents described herein are suitable for administration to the subject. It is to be understood that depending on the types of tumor to be treated, different immunotherapeutic agents may be administered. The skilled clinician in the art is able to identify the appropriate immunotherapeutic agents. In some embodiments, immune checkpoint inhibitors, e.g., anti PD-1, anti-PD-L1, and/or anti-CTLA-4 antibodies, are administered.

Types of tumor that may be treated using the compositions and methods of the present disclosure include, without limitation, premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

In some embodiments, the tumor has metastasized and has a cutaneous or surface exposed tumor lesion (e.g. Merkel cell carcinoma, head and neck squamous cell carcinoma, basal cell carcinoma, breast carcinoma and metastatic breast carcinoma, cutaneous T cell lymphoma (Sezary syndrome) and sarcoma). In some embodiments, the tumor is accessible without surgical intervention, e.g., tumors located in the head, neck, cervix, larynx, esophagus or skin. In some embodiments, the tumor is cancerous or malignant. In some embodiments, the tumor is made accessible (made accessible to light/laser) by surgical or endoscopic intervention. In some embodiments, the tumor is metastatic. In some embodiments, the tumor is a primary tumor and has metastasized. In some embodiments, the metastatic cancer has a cutaneous or surface exposed tumor lesion. In some embodiments, the tumor has a lesion that is accessible to treatment with an infrared laser. In some embodiments, the metastatic cancer has a tumor lesion or metastasis in the eye. In some embodiments, the tumor is an ocular tumor and has metastasized to the liver. When the tumor is an ocular tumor or has metastasized to the eye, the ocular tumor is located in the vitreous, choroidal space, iris, ciliary body, sclera, fovea, retina, optic disk, or optic nerve.

A subject having a tumor, in some embodiments, is a mammal, such as a human.

The compositions and/or the therapeutic agents of the present disclosure are administered to the subject in an effective amount to reduce or prevent cancer growth. "An effective amount" as used herein refers to the amount of each agent required to confer therapeutic effect on the subject, either alone or in combination with one or more other agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, agents that are compatible with the human immune system, such as agents comprising regions from humanized antibodies or fully human antibodies, may be used to prolong half-life of the compound and to prevent the compound being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a compound may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the compound used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the compound is administered for preventive or therapeutic purposes, previous therapy, the subject's clinical history and response to the antagonist, and the discretion of the attending physician. Typically the clinician will administer an agent until a dosage is reached that achieves the desired result. Administration of one or more agents can be continuous or intermittent, depending, for example, upon the recipient's physiological condition, whether the purpose of the administration is therapeutic or prophylactic, and other factors known to skilled practitioners. The administration of an agent may be essentially continuous over a preselected period of time or may be in a series of spaced dose, e.g., either before, during, or after developing a disease.

As used herein, the term "treating" refers to the application or administration of a agent or composition including the agent to a subject, who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

The present disclosure also encompasses the following numbered paragraphs:

1. A method comprising
   (a) administering, to a subject having a tumor, a composition comprising tumor-targeting viral capsid protein assemblage that comprises photosensitive molecules conjugated to viral capsid proteins of the assemblage; and
   (b) administering to the subject having a tumor, a composition comprising an immune checkpoint inhibitor.
2. The method of paragraph 1, wherein the viral capsid proteins are human papillomavirus capsid proteins.
3. The method of paragraph 1, wherein the viral capsid proteins are non-human papillomavirus capsid proteins.
4. The method of paragraph 3, wherein the non-human papillomavirus capsid proteins are bovine papillomavirus capsid proteins or cottontail papillomavirus proteins.
5. The method of any one of paragraphs 1-4, wherein the viral capsid proteins comprise papillomavirus L1 capsid proteins or a combination of papillomavirus L1 capsid proteins and papillomavirus L2 capsid proteins.
6. The method of any one of paragraphs 1-5, wherein the tumor-targeting viral capsid protein assemblage is a capsomere or a virus-like particle.
7. The method of any one of paragraphs 1-6, wherein the tumor-targeting viral capsid protein assemblage comprises 10 to 1000 photosensitive molecules, optionally wherein the tumor-targeting viral capsid protein assemblage comprises 200 to 500 photosensitive molecules.
8. The method of any one of paragraphs 1-7, wherein the photosensitive molecules comprise a fluorescent dye, an infrared (IR) dye, a near infrared (NIR) dye, porphyrin, chlorophyll, chlorin, phthalocyanine, bacteriochlorin, texaphyrin, porfimer sodium, verteporfin, temoporfin, talaporfin, methylene blue, amino levulinic acid, or a combination thereof.
9. The method of any one of paragraphs 1-8, wherein the tumor-targeting viral capsid protein assemblage is a virus-like particle comprising 72 capsomeres assembled from variant or modified HPV 16/31 L1 capsid proteins and wild-type HPV L2 capsid proteins, and wherein the photosensitive molecules comprise IRdye 700DX.
10. The method of any one of paragraphs 1-9, wherein the immune checkpoint inhibitor inhibits binding of CTLA-4, PD-1, PD-L1, TIM3, LAGS, B7-H3, B7-H4, BTLA, GALS, Chk1 or A2aR to a cognate binding partner.
11. The method of paragraph 10, wherein the immune checkpoint inhibitor is an antibody.
12. The method of paragraph 11, wherein the antibody is a monoclonal antibody.

13. The method of any one of paragraphs 1-12, wherein the antibody is selected from an anti-CTLA-4 antibody, an anti-PD-1 antibody, an anti-PD-L1 antibody, an anti-TIM3 antibody, an anti-LAG3 antibody, an anti-B7-H3 antibody, an anti-B7-H4 antibody, an anti-BTLA antibody, an anti-GALS antibody, an anti-Chk1 antibody, an anti-A2aR antibody, and a combination of any two or more of the foregoing antibodies.
14. The method of paragraph 13, wherein the antibody is selected from pembrolizumab, nivolumab, ipilimumab and any combination of two or more of the foregoing antibodies.
15. The method of any one of paragraphs 1-14, wherein the tumor-targeting viral capsid protein assemblage and the immune checkpoint inhibitor are administered concurrently.
16. The method of any one of paragraphs 1-14, wherein the tumor-targeting viral capsid protein assemblage and the immune checkpoint inhibitor are administered sequentially.
17. The method of paragraph 16, wherein the tumor-targeting viral capsid protein assemblage is administered to the subject before the immune checkpoint inhibitor is administered to the subject.
18. The method of paragraph 16 and 17, wherein the tumor-targeting viral capsid protein assemblage is administered locally to a tumor or tumor lesion, and wherein the immune checkpoint inhibitor is administered systemically.
19. The method of any one of paragraphs 1-18, wherein the tumor-targeting viral capsid protein assemblage and/or the immune checkpoint inhibitor is administered by injection, topically, or by implantation.
20. The method of paragraph 19, wherein the injection is intralesional injection, subcutaneous injection, intravitreal injection, suprachoroidal injection, intraperitoneal injection, intra-arterial injection, intra-hepatic injection, intravesical injection, or any combination thereof.
21. The method of any one of paragraphs 1-20 further comprising activating the photosensitive molecules using an infrared laser, a near-infrared laser, or an ultraviolet laser.
22. The method of any one of paragraphs 1-21, wherein the tumor is cancerous.
23. The method of paragraph 23, wherein the tumor is metastatic.
24. The method of any one of paragraphs 1-23, wherein the tumor is a melanoma, carcinoma, sarcoma or lymphoma.
25. The method of any one of paragraphs 1-24, wherein the tumor has a lesion that is accessible to treatment with an infrared laser.
26. The method of paragraph 25, wherein the tumor is a Merkel cell carcinoma, a squamous cell carcinoma, a basal cell carcinoma, a metastatic breast carcinoma, a cutaneous T cell lymphoma or a sarcoma.
27. The method of any one of paragraphs 1-25, wherein the tumor is a primary tumor and has metastasized.
28. The method of any one of paragraphs 1-27, wherein the tumor is located in and/or has metastasized to the liver, bladder, eye, head, neck, cervix, larynx, skin, lung, pleura, pancreas, stomach, esophagus, colon, breast, ovary, prostate, testis, brain, meninges, kidney.
29. The method of any one of paragraphs 1-27, wherein the subject is human.

30. A method comprising administering an immune checkpoint inhibitor to a subject having a tumor who is undergoing treatment with a tumor-targeting viral capsid protein assemblage that comprises photosensitive molecules conjugated to viral capsid proteins of the assemblage.

31. A composition comprising an immune checkpoint inhibitor and a tumor-targeting viral capsid protein assemblage that comprises photosensitive molecules conjugated to viral capsid proteins of the assemblage.

32. The composition of paragraph 31, wherein the viral capsid proteins are human papillomavirus capsid proteins.

33. The composition of paragraph 31, wherein the viral capsid proteins are non-human papillomavirus capsid proteins.

34. The composition of paragraph 33, wherein the non-human papillomavirus capsid proteins are bovine papillomavirus capsid proteins or cottontail papillomavirus proteins.

35. The composition of any one of paragraphs 31-34, wherein the viral capsid proteins comprise papillomavirus L1 capsid proteins or a combination of papillomavirus L1 capsid proteins and papillomavirus L2 capsid proteins.

36. The composition of any one of paragraphs 31-35, wherein the tumor-targeting viral capsid protein assemblage is a capsomere or a virus-like particle.

37. The composition of any one of paragraphs 31-36, wherein the tumor-targeting viral capsid protein assemblage comprises 10 to 1000 photosensitive molecules.

38. The composition of any one of paragraphs 31-37, wherein the photosensitive molecules comprise a fluorescent dye, an infrared (IR) dye, a near infrared (NIR) dye, porphyrin, chlorophyll, chlorin, phthalocyanine, bacteriochlorin, texaphyrin, porfimer sodium, verteporfin, temoporfin, talaporfin, methylene blue, amino levulinic acid, or a combination thereof.

39. The composition of any one of paragraphs 31-38, wherein the tumor-targeting viral capsid protein assemblage is a virus-like particle comprising 72 capsomeres assembled from variant or modified HPV 16/31 L1 capsid proteins and wild-type HPV L2 capsid proteins, and wherein the photosensitive molecules comprise IRdye 700DX.

40. The composition of any one of paragraphs 31-39, wherein the immune checkpoint inhibitor inhibits binding of CTLA-4, PD-1, PD-L1, TIM3, LAGS, B7-H3, B7-H4, BTLA, GALS, Chk1 or A2aR to a cognate binding partner.

41. The composition of paragraph 40, wherein the immune checkpoint inhibitor is an antibody.

42. The composition of paragraph 41, wherein the antibody is a monoclonal antibody.

43. The composition of any one of paragraphs 31-42, wherein the antibody is selected from an anti-CTLA-4 antibody, an anti-PD-1 antibody, an anti-PD-L1 antibody, an anti-TIM3 antibody, an anti-LAG3 antibody, an anti-B7-H3 antibody, an anti-B7-H4 antibody, an anti-BTLA antibody, an anti-GALS antibody, an anti-Chk1 antibody, an anti-A2aR antibody, and a combination of any two or more of the foregoing antibodies.

44. The composition of paragraph 43, wherein the antibody is selected from pembrolizumab, nivolumab, ipilimumab and any combination of two or more of the foregoing antibodies.

The present disclosure is further illustrated by the following Examples, which in no way should be construed as further limiting.

EXAMPLES

Example 1: Efficacy and Induction of Anti-Tumor Immune Response Using Intravenous-Administered VLP Conjugate Methods Albino C57Bl/6 mice were injected subcutaneously with $5 \times 10^5$ TC-1 cells as part of a lung cancer model. When tumors reached ~100-300 mm³, designated as day 0, the animals were administered 25 μg a VLP conjugate (a tumor-targeting VLP conjugated to IRDye®700DX) or PBS via intravenous injection followed by tumor-targeted near-IR light treatment (50 J/cm²; 690 nm) 12 hours later. This protocol was repeated on day 3. Blood was drawn on days 0 and 17 to measure tumor specific T-cell responses. Animals were euthanized when tumors reached>1500 mm³ in size.

Results

Figure 3:
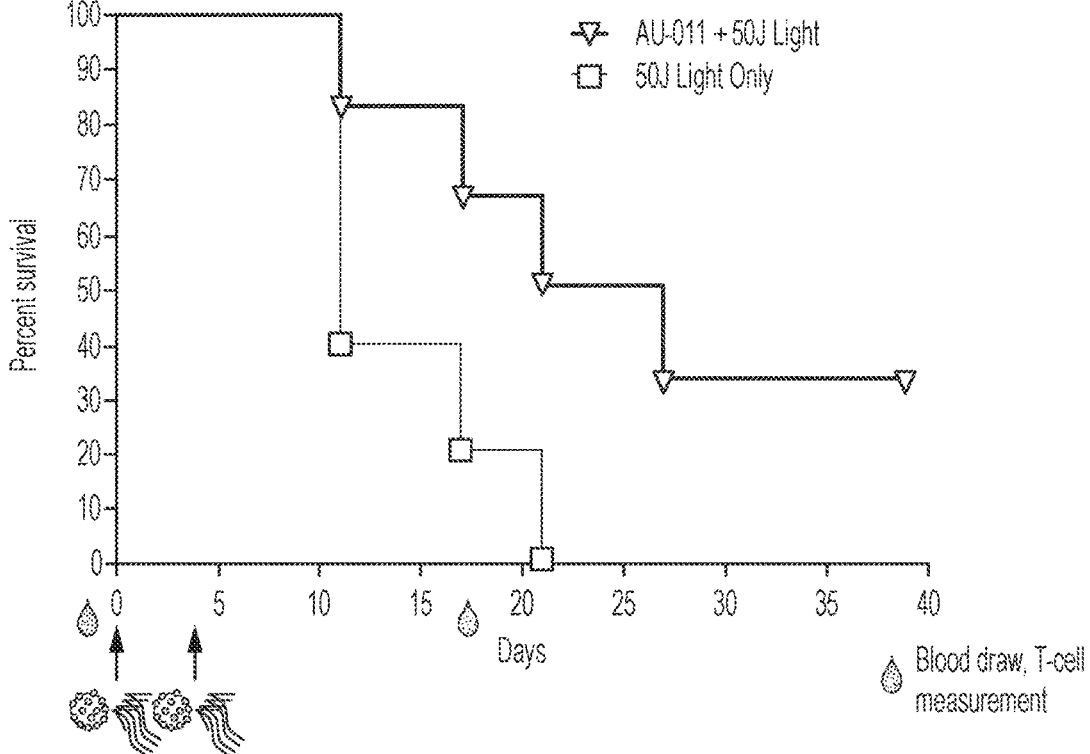
FIG. 3 is a graph showing the survival curves of mice in a TC-1 model. After tumors of $\sim$100-300 mm$^3$ formed (day 0), the mice were injected with the VLP conjugate or PBS and then treated with light 12 hours later. The protocol was repeated on day 3. Blood was drawn on days 0 and 17 to measure tumor-specific T-cell responses.
Figure 4:
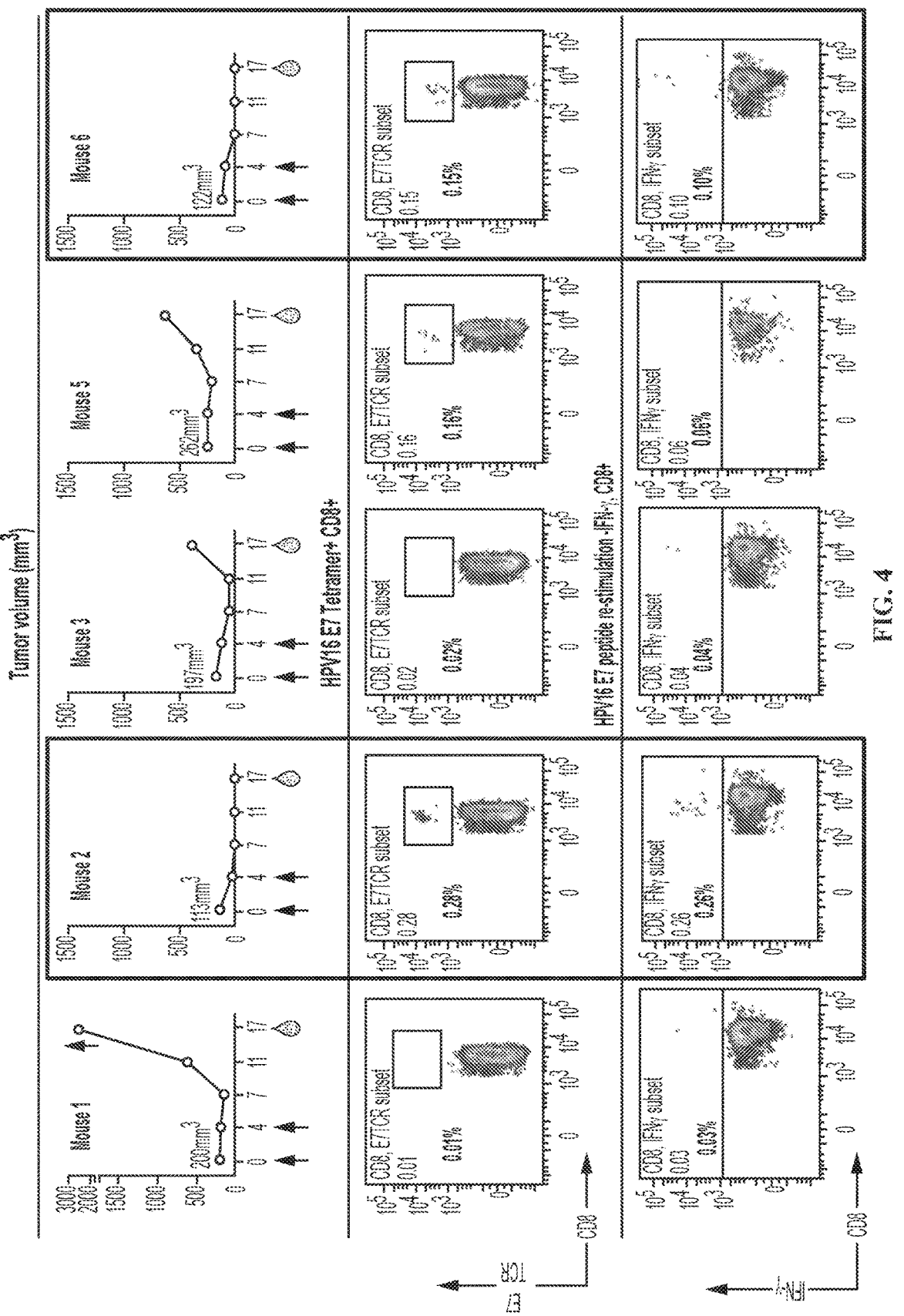
FIG. 4 shows tumor-antigen-specific CD8$^+$ T-cells detected in the blood of experimental mice at day 17. Tumor volume, HPV16 E7 tetramer$^+$ CD8$^+$ gating, and HPV16 E7 peptide re-stimulation $-$IFN-$\gamma$, CD8$^+$ gating are shown.
Figure 5:
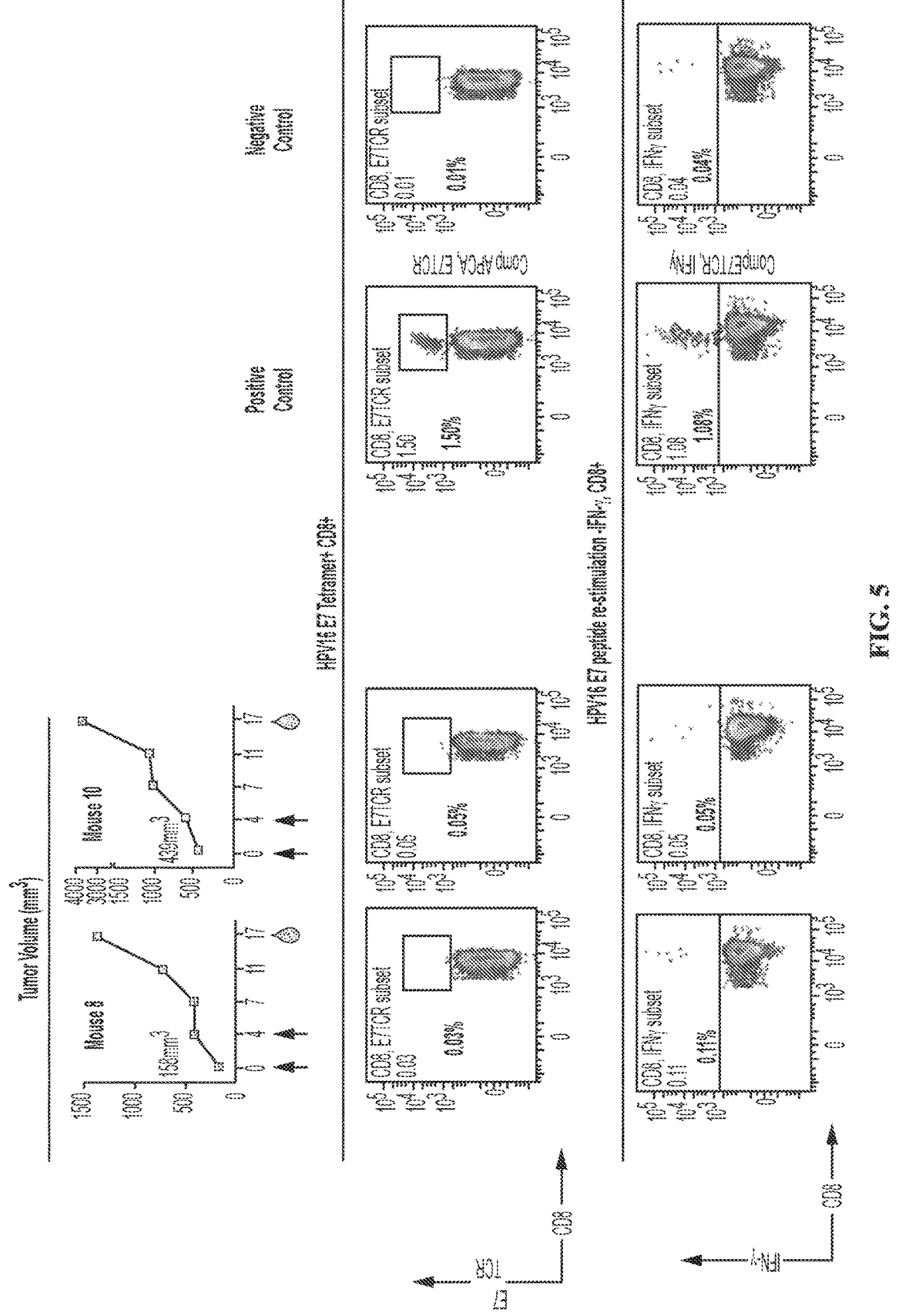
FIG. 5 illustrates that light treatment alone does not result in tumor-antigen-specific CD8$^+$ T-cells. Tumor volume, HPV16 E7 tetramer$^+$ CD8$^+$ gating, and HPV16 E7 peptide re-stimulation $-$IFN-$\gamma$, CD8$^+$ gating are shown.

There was an overall significant increase in survival in VLP conjugate/light treated compared with PBS treated animals, with all control animals being euthanized by day 21 with a median survival of 11 days. VLP conjugate/light treated animals survived a median of 24 days and two animals displayed complete tumor regression (FIG. 3 and Table 2). Tumor-specific CD8+ T-cells (E7 tetramer-positive and IFN-gamma secretion after E7 peptide stimulation) were detected in these same two animals indicating that the VLP conjugate was capable of eliciting anti-tumor immunity to neo-tumor antigens (FIG. 4). Animals with smaller tumors controlled tumor growth, and an E7-specific immune response were detected by day 17. At the time of treatment, the tumor burden was higher than in typical experiments and the two responding animals also had the smallest tumors at the onset of treatment, indicating that there may be a treatment threshold. Light treatment alone was shown to be ineffective (FIG. 5). Therefore, in an animal model of aggressive lung cancer (immune-competent), the combined treatment showed good efficacy (two complete responses). Tetramer staining and cytokine secretion in response to stimulation with the E7 peptide demonstrated the initiation of anti-tumor immunity.

TABLE 1

| Median Survival in TC-1 Model | | |
| --- | --- | --- |
| Group | n | Median Survival (Days) |
| Light only | 5 | 11 |
| VLP conjugate + light | 7 | 24 (p = 0.05; Log-rank test) |

Example 2: Efficacy and Induction of Anti-Tumor Immune Response Using IV-Administered VLP-Conjugate in a New Formulation Buffer Methods Albino C57Bl/6 mice were injected subcutaneously with $5 \times 10^5$ TC-1 cells as part of a lung cancer model. When tumors reached ~50 mm³, designated as day 0, the animals were administered 100 µg VLP conjugate or PBS via intravenous injection followed by tumor-directed near-IR light treatment (50 J/cm²; 690 nm) 12 and 24 hours later. Two additional arms were included, no treatment and VLP conjugate without light. This protocol was repeated on day 3. Blood was drawn on days 0 and 17 to measure tumor-specific T-cell responses. Animals were euthanized when tumors reached>1500 mm³ in size.

Naïve mice and mice displaying tumor regression were subcutaneously challenged with 5×10⁵ TC-1 cells on their opposing flank and tumor burden measured for one month. Animals re-challenged with TC-1 cells did not exhibit tumor growth following re-challenge, while all control animals that were re-challenged had tumor growth.

Results

Figure 2:
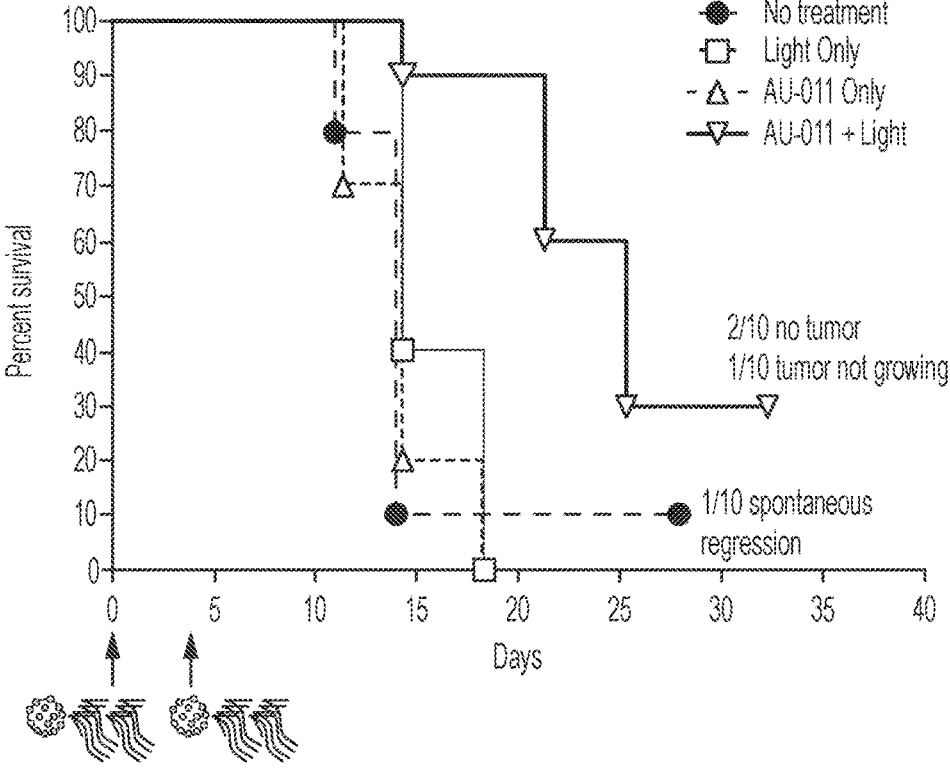
FIG. 2 is a graph showing the survival curves of mice in a TC-1 model. After tumors of $\sim$50 mm$^3$ formed (day 0), the mice were injected with the VLP conjugate or phosphate buffered saline (PBS) and then treated with light at 12 and 24 hours later. The protocol was repeated on day 3.

There was an overall significant increase in survival in the VLP conjugate/light group compared with all other arms in the animal model of aggressive lung cancer (immune-competent) (FIG. 2 and Table 2). One animal in the untreated group displayed spontaneous regression. Two VLP conjugate/light mice displayed complete regression and one mouse showed controlled growth, in that the tumor shrank in size and did not grow or clear. Therefore, the combined treatment showed good efficacy. The anti-tumor response that was generated was capable of preventing new tumor outgrowth upon challenge.

E7 tetramer staining and IFN-gamma secretion could be detected in two animals. The background staining was high however, so it is possible that low positive values were masked. The four remaining mice were subsequently challenged with TC-1 tumors alongside three naïve mice. By the time the naïve mice had to be euthanized due to tumor burden, ¾ challenged mice remained tumor-free. The only animal to not survive tumor challenge was the mouse that displayed tumor control (no growth). The challenge tumor did not grow; however, the primary tumor was no longer controlled and began to grow again. These data indicate that an immunological response was made and was capable of not only removing primary tumors, but also able to prevent occurrence of a later tumor. The alteration in VLP conjugate buffer may have led to decreased stability after IV injection leading to fewer responders.

TABLE 2

| Median Survival in TC-1 Model | | |
| --- | --- | --- |
| Group | n | Median Survival (Days) |
| No treatment | 10 | 14 |
| Light only | 10 | 14 |
| VLP conjugate only | 10 | 14 |
| VLP conjugate + light | 10 | 25 (p < 0.0005; Log-rank test) |

Example 3: Combination of VLP Conjugate with Existing Cancer Therapies to Enhance the Generation of Tumor Specific T-Cells

Background

Several classes of cancer therapies drive tumor cells towards apoptotic death, which is often ignored by the host immune response. Additionally, many tumors have evolved to evade immune recognition by the host. In light of this, a new generation of immune modulators/checkpoint inhibitors has been introduced. Namely antibodies against T-cell and tumor cell surface antigens that block inhibitory signals passing between the cells (e.g. PD-1, PD-L1, CTLA-4) (Melero, 2015). Data indicate that the VLP conjugate is capable of inducing anti-tumor immunity, likely due to acute necrotic death. Combining it with a treatment modality which enhances the T-cell/tumor interaction significantly increases its efficacy against the primary tumor and leads to systemic anti-tumor immunity, thus potentially targeting unidentified distant metastases and preventing recurrence of disease.

Methods

Figure 6:
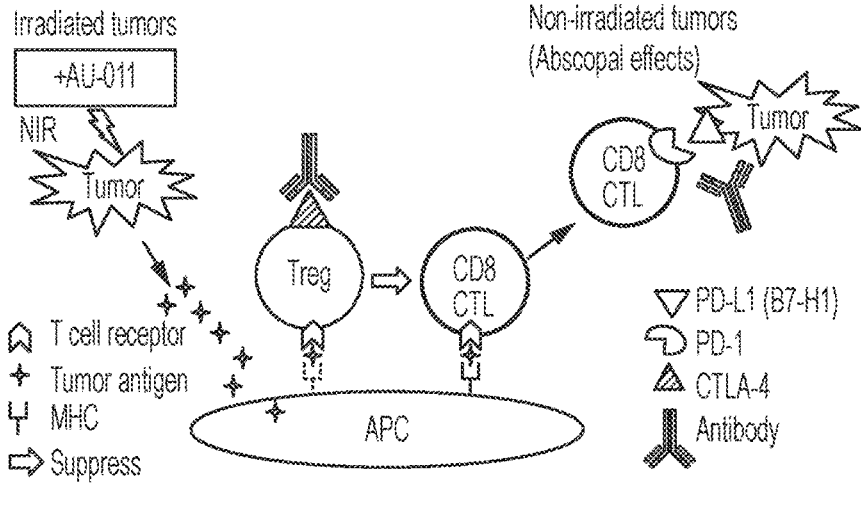
FIG. 6 is a schematic illustrating the combination of a tumor-targeted drug conjugate activated with NIR, and checkpoint inhibitors to prevent tumor growth and recurrence.

Using the TC-1 tumor model, VLP conjugate/light treatment is combined with anti-PD-1, anti-PD-L1 and/or anti-CTLA-4 (or other molecules as appropriate). Control arms include animals receiving these antibodies or VLP conjugates alone. VLP conjugate/light treatment is highly destructive to the tumor microenvironment immediately after treatment. This, combined with the knowledge that it takes an estimate of two weeks to generate a tumor specific T-cell response, means that the immune checkpoint inhibitors are applied prior to and/or after VLP conjugate/light treatment to evaluate the synergistic effects on tumor response. Read-outs are survival and measurement of tumor specific T-cells in circulation at bi-weekly intervals post-treatment. A VLP conjugate plus a checkpoint inhibitor treatment is more effective at controlling tumor growth and inducing antitumor immunity when compared to the same checkpoint inhibitor or the VLP conjugate as a single treatment (FIG. 6).

Example 4: Subcutaneous Model

Figure 7:
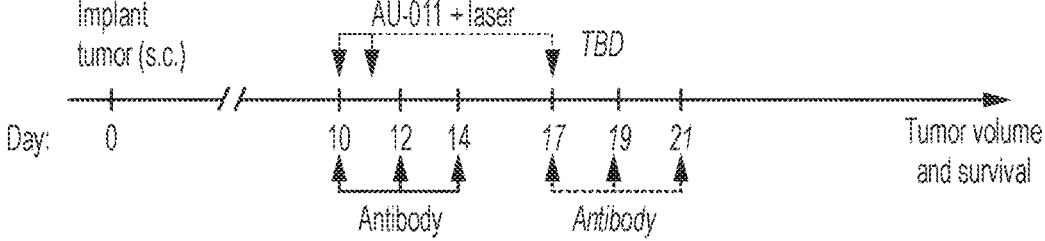
FIG. 7 is a schematic of the experiment performed in Example 4.

Mice will be implanted with either TC-1 (lung) or MB49 (bladder) cancer cells (1-5×10⁵). When tumors reach ~50 mm³ (appx. 10 days), they will receive i.p. 100 µg antibody (a CTLA-4, α PD-L1 or α PD-1 and the corresponding isotype control) i.v.100-200 µg tumor-targeting virus-like particles (VLP) having photosensitive molecules (IRDye®700DX) conjugated to the primary amines in the surface of the VLP (drug), followed 12 hr later by 690 nm light (50 J/cm²) (FIG. 7).

Antibody will be administered two more times, two days apart.

Drug and 69 0 nm light exposure will be repeated after 24 hr.

A second round of drug/light and antibody treatment may be administered after one week.

Antibodies—delivered i.p. 100 µg; sourced from BioX-Cell

α CTLA-4—clone 9D9

α PD-L1—clone 10F.9G2

α PD-1—clone RMP1-14

Isotype controls

REFERENCES

Feltkamp M C, Smits H L, Vierboom M P, Minnaar R P, de Jongh B M, Drijfhout J W, ter Schegget J, Melief C J, Kast W M. Vaccination with cytotoxic T lymphocyte epitope-containing peptide protects against a tumor induced by human papillomavirus type 16-transformed cells. Eur J Immunol. 1993 September; 23(9):2242-9.

Lin K Y, Guarnieri F G, Staveley-O'Carroll K F, Levitsky H I, August J T, Pardoll D M, Wu T C. Treatment of established tumors with a novel vaccine that enhances major histocompatibility class II presentation of tumor antigen. Cancer Res. 1996 Jan. 1; 56(1):21-6.

Melero I, Berman D M, Aznar M A, Korman A J, Perez Gracia J L, Haanen J. Evolving synergistic combinations of targeted immunotherapies to combat cancer. Nat Rev Cancer. 2015 August; 15(8):457-72.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The term "or" is generally employed in its sense including "and/or" unless the content clearly dictates otherwise.

It should be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended (including but not limited to). Only the transitional phrases "consisting of" and "consisting essentially of" shall be closed or semi-closed transitional phrases, respectively, as set forth in the United States Patent Office Manual of Patent Examining Procedures, Section 2111.03. It should also be understood that all open-ended transitional phrases may be substituted with closed or semi-closed transitional phrases. Thus, the term "comprising" may be substituted with "consisting of" or "consisting essentially of."

What is claimed is:

1. A method for treating a bladder tumor, comprising:
(a) administering to a primary bladder tumor in a subject a composition comprising a virus-like particle conjugate that comprises (i) human papillomavirus capsid proteins and photosensitive molecules, wherein the photosensitive molecules are conjugated to the human papillomavirus capsid proteins, wherein the composition is administered via intralesional injection;
(b) administering to the primary bladder tumor in the subject a composition comprising an immune checkpoint inhibitor selected from anti-PD-1 antibodies, anti-CTLA-4 antibodies, and anti-LAG3 antibodies, wherein the immune checkpoint inhibitor is administered via intravenous or intravesical injection; and
(c) activating the photosensitive molecules using an infra-red laser, a near-infrared laser, or an ultraviolet laser.

2. The method of claim 1, wherein the human papillomavirus capsid proteins comprise papillomavirus L1 capsid proteins.

3. The method of claim 2, wherein the human papillomavirus capsid proteins comprise a combination of human papillomavirus L1 capsid proteins and human papillomavirus L2 capsid proteins.

4. The method of claim 1, wherein the virus-like particle conjugate comprises 10 to 1000 photosensitive molecules.

5. The method of claim 4, wherein the virus-like particle conjugate comprises about 200 photosensitive molecules.

6. The method of claim 1, wherein the photosensitive molecules comprise an infrared (IR) dye.

7. The method of claim 1, wherein the photosensitive molecules comprise a near infrared (NIR) dye.

8. The method of claim 1, wherein the photosensitive molecules comprise a phthalocyanine dye.

9. The method of claim 1, wherein the immune checkpoint inhibitor is pembrolizumab.

10. The method of claim 1, wherein the immune checkpoint inhibitor is nivolumab.

11. The method of claim 1, wherein the immune checkpoint inhibitor is ipilimumab.

12. The method of claim 1, wherein the primary bladder tumor is cancerous.

13. The method of claim 1, wherein the primary bladder tumor is a melanoma, carcinoma, sarcoma or lymphoma.

14. The method of claim 1, wherein the composition comprising an immune checkpoint inhibitor is administered via intravenous injection.

15. A method for treating a bladder tumor, comprising:
(a) administering to a primary bladder tumor in a subject a composition comprising a virus-like particle conjugate that comprises (i) human papillomavirus capsid proteins and photosensitive infrared dye molecules, wherein the photosensitive molecules are conjugated to the human papillomavirus capsid proteins, wherein the composition is administered via intralesional injection;
(b) administering to the primary bladder tumor in the subject a composition comprising an immune checkpoint inhibitor selected from pembrolizumab, nivolumab, and ipilimumab, wherein the immune checkpoint inhibitor is administered via intravenous or intravesical injection; and
(c) activating the photosensitive infrared dye molecules using an infrared laser.

16. The method of claim 15, wherein the human papillomavirus capsid proteins comprise a combination of human papillomavirus L1 capsid proteins and human papillomavirus L2 capsid proteins.

17. The method of claim 15, wherein the virus-like particle conjugate comprises 10 to 1000 photosensitive molecules.

18. The method of claim 17, wherein the virus-like particle conjugate comprises about 200 photosensitive molecules.

19. The method of claim 15, wherein the primary bladder tumor is a melanoma, carcinoma, sarcoma or lymphoma.

20. The method of claim 15, wherein the composition comprising an immune checkpoint inhibitor is administered via intravenous injection.

* * * * *